(12) United States Patent
Bregulla (10) Patent No.: US 8,850,684 B2
(45) Date of Patent: Oct. 7, 2014

(54) SYSTEM AND METHOD FOR CRIMPING BODY LUMEN FILTERS

(75) Inventor: Rainer Bregulla, Balingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 579 days.

(21) Appl. No.: 13/133,112

(22) PCT Filed: Dec. 16, 2009

(86) PCT No.: PCT/EP2009/009048
§ 371 (c)(1),
(2), (4) Date: Sep. 22, 2011

(87) PCT Pub. No.: WO2010/078931
PCT Pub. Date: Jul. 15, 2010

(65) Prior Publication Data
US 2012/0005876 A1 Jan. 12, 2012

Related U.S. Application Data

(60) Provisional application No. 61/138,416, filed on Dec. 17, 2008.

(51) Int. Cl.
*B21D 39/00* (2006.01)
*A61M 29/00* (2006.01)
*A61F 2/01* (2006.01)
*A61F 2/95* (2013.01)

(52) U.S. Cl.
CPC .......... *A61F 2/01* (2013.01); *A61F 2002/9522* (2013.01); *A61F 2002/011* (2013.01); *A61F 2230/0023* (2013.01); *A61F 2002/016* (2013.01)
USPC ............................................ 29/508; 606/200

(58) Field of Classification Search
CPC ..... A61F 2/01; A61F 2/848; A61F 2002/011; A61F 2002/016; A61F 2230/005; A61F 2230/0067; A61F 2230/0078; A61F 2002/9522; A61F 2230/0023; A61F 2/95; A61F 2/958; A61F 2/013; A61B 17/12022
USPC .......................... 29/505, 508, 515, 516, 812; 606/200.108, 194
See application file for complete search history.

(56) References Cited

U.S. PATENT DOCUMENTS

| 5,893,852 A | 4/1999 | Morales |
| 2003/0208227 A1 | 11/2003 | Thomas |

FOREIGN PATENT DOCUMENTS

| EP | 0941713 | 9/1999 |
| WO | WO 01/35861 | 5/2001 |
| WO | WO 2010/078931 | 7/2010 |

OTHER PUBLICATIONS

U.S. Appl. No. 61/138,416, filed Dec. 7, 2008, Bregulla.

*Primary Examiner* — John C Hong
(74) *Attorney, Agent, or Firm* — Workman Nydegger; Jonathan Feuchtwang (57) ABSTRACT

As described herein, a body lumen filter is provided that includes a body configured to move between a pre-deployed state and a deployed state, a filtering structure operatively associated with the body to filter particulates, and a blending structure operatively associated with the body. The blending structure can be configured to break up at least one of the particulates.

22 Claims, 8 Drawing Sheets

SYSTEM AND METHOD FOR CRIMPING BODY LUMEN FILTERS

CROSS-REFERENCE TO RELATED APPLICATIONS

This Patent Application is a U.S. National Stage of International Application No. PCT/EP2009/009048, filed Dec. 16, 2009, which claims the benefit of and priority to U.S. Provisional Patent Application having Ser. No. 61/138,416, filed on Dec. 17, 2008, the disclosures of which are incorporated herein by reference in their entireties.

BACKGROUND

1. Field of the Invention

The present disclosure relates to medical devices and to body lumen filters in particular, such as a system and method for crimping body lumen filters.

2. Background and Relevant Art

Surgical procedures, including both invasive as well as minimally-invasive procedures, save countless lives each year. However, the instruments and processes used during such procedures sometimes create additional challenges. For example, many minimally invasive procedures are performed using highly specialized surgical tools that are introduced to the procedure site by way of the patient's vasculature. In particular, a catheter is introduced into the vasculature by way of small incision. The catheter is then advanced into proximity with the procedure site. Thereafter, the surgical tools are advanced to the procedure site through the catheter. With the surgical tools thus at the procedure site, the surgical tools are then manipulated from the outside of the body. Accordingly, a surgical procedure can be performed with only a small incision. While such an approach can reduce the invasiveness of performing a surgical procedure, this approach can cause additional challenges.

In particular, as the catheter and/or surgical devices are advanced through the vasculature, their passage can cause arterial plaques, clots, or other debris commonly referred to as emboli to become dislodged and move with the blood as it circulates through the vasculature. As the emboli move downstream, they can encounter plaque or other obstructions within the bloodstream to form new clots or obstructions in the bloodstream. Such obstructions can result in partial or complete blockage of vessels supplying blood and oxygen to critical organs, such as the heart, lungs and brain.

Accordingly, filter devices have been developed to capture the emboli at safe locations. Conventional implantable blood filters that have a variety of geometries are known. Many are generally basket or cone shaped, in order to provide an adequate clot-trapping area while permitting sufficient blood flow. Also known are filters formed of various loops of wire, including some designed to partially deform the vessel wall in which they are implanted.

One of the challenges with implanting vena cava filters includes preventing the vena cava filter from migrating or otherwise becoming displaced from its deployed position. Migration of the device can result in decreased filtering efficiency or other undesirable effects as the device moves from its intended location. In order to maintain the filters at the intended location, many vena cava filters include anchors that engage the tissue. These anchors often pierce the tissue to thereby prevent migration of the vena cava filter. If the anchors pierce too deeply, the tissue can be damaged.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A device for crimping a body lumen filter can include a plug having an outer angled surface and a base having a channel defined therein. The base further includes an inner angled surface in communication with the channel and extending away from the channel such that at least a portion of the inner angled surface and the outer angled surface are complimentary.

A system can include a crimping device having a plug and a base having a channel defined therein. The body lumen filter can be configured to be located at least partially between the base and the plug. The system can also include a deployment device having an outer tube and a retrieval device in which the retrieval device is configured to draw the body lumen filter through the channel and at least partially into the outer tube while the crimping device is configured to apply even pressure to the body lumen filter between the base and the plug as the body lumen filter is drawn through the channel.

These and other features of the present invention will become more fully apparent from the following description and appended claims, or can be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Devices, systems, and methods are provided herein for loading and deploying vascular devices, such as body lumen filters. By way of example only, a body lumen may include a blood vessel. Filtering may be performed by body lumen filters. For instance, embodiments of body lumen filters (e.g. including vena cava and/or other lumen filters), are described. Components of body lumen filters also are described. These components may include anchors and/or other components. By way of example only, a body lumen may include a blood vessel. Filtering may be performed by body lumen filters. For instance, embodiments of body lumen filters (e.g. including vena cava and/or other lumen filters), are described. Components of body lumen filters also are described. These components may include anchors and/or other components. In at least one example, a device is provided for loading a vascular device into a deployment device that includes complimentary shaped and angled components. In particular, a device can include a base with at least one angled interior surface defining a cavity and a plug with at least one complimentary exterior surface. The exterior angled surface and interior angled surfaces may be oriented at a similar or the same angle. The device can further include a channel in communication with the cavity. A generally tubular extension defining a lumen can be coupled to the base portion in such a manner that the lumen is in communication with the channel.

The vascular device can be positioned on the base and the plug can be inserted into the vascular device. The plug can then be urged toward the base to apply pressure to the body lumen filter. The angle surfaces described above can correspond closely the shape of a vascular device in an deployed state. Such a configuration can result in even distribution of pressure on the vascular device. While the pressure on the vascular device is thus applied, the vascular device can be drawn through the channel and into a deployment device. The even application of pressure on the vascular device can reduce unintended deformation of the structure of the vascular device as the vascular device is loaded into the deployment device. This in turn can help maintain the shape of the deployment device until deployment, which can help ensure the vascular device functions as intended once deployed.

The vascular devices and body lumen filters described herein may be manufactured from any suitable material. For example, a body lumen filter and/or vascular device may be, at least partially, formed from various materials including nickel titanium and/or alloys thereof, cobalt chromium and/or alloys thereof, other materials, and/or combinations thereof.

These materials may include at least one beneficial agent incorporated into the material and/or coated over at least a portion of the material. The beneficial agents may be applied to body lumen filters that have been coated with a polymeric compound. Incorporation of the compound or drug into the polymeric coating of the body lumen filter can be carried out by dipping the polymer-coated body lumen filter into a solution containing the compound or drug for a sufficient period of time (such as, for example, five minutes) and then drying the coated body lumen filter, preferably by means of air drying for a sufficient period of time (such as, for example, 30 minutes). The polymer-coated body lumen filter containing the beneficial agent may then be delivered to a body vessel.

The pharmacologic agents that can be effective in preventing restenosis can be classified into the categories of anti-proliferative agents, anti-platelet agents, anti-inflammatory agents, anti-thrombotic agents, and thrombolytic agents. Anti-proliferative agents may include, for example, crystalline rapamycin. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids.

Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

One or more immunosuppressant agents may be used. Immunosuppressant agents may include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins. In addition, a crystalline rapamycin analog, A-94507, SDZ RAD (a.k.a. Everolimus), and/or other immunosuppressants.

Figure 1:
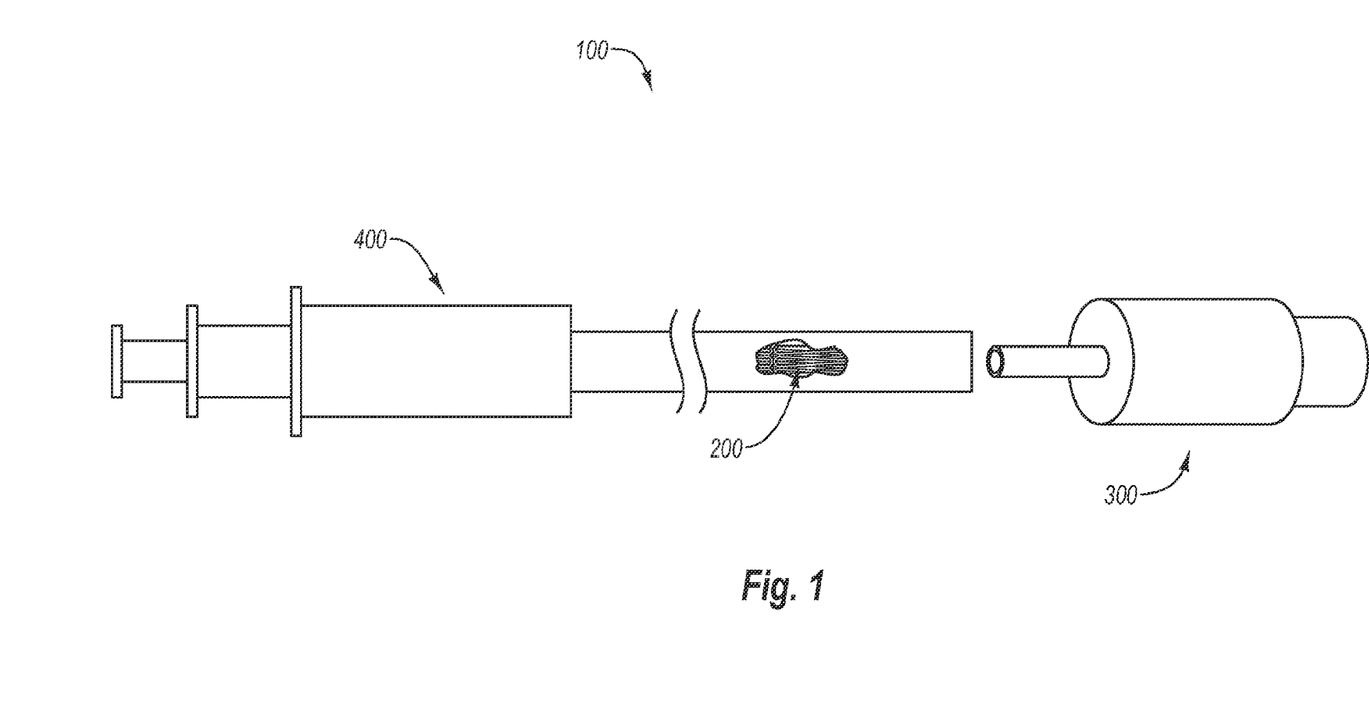
FIG. 1 illustrates a system for deploying a body lumen filter according to one example.

FIG. 1 illustrates a system 100 for loading and deploying a body lumen filter 200. The system 100 generally includes a crimping device 300 and a deployment device 400. The crimping device 300 cooperates with the deployment device 400 to thereby position the body lumen filter 200 in the pre-deployed state shown within the deployment device 400. The deployment device 400 then deploys the body lumen filter 200 at a deployment site. One exemplary body lumen filter 200 will first be described followed by the exemplary crimping device 300, followed by a description of a method of using the body lumen filter that includes loading the body lumen filter in the deployment device and using the deployment device to deploy the body lumen filter.

Figure 2A:
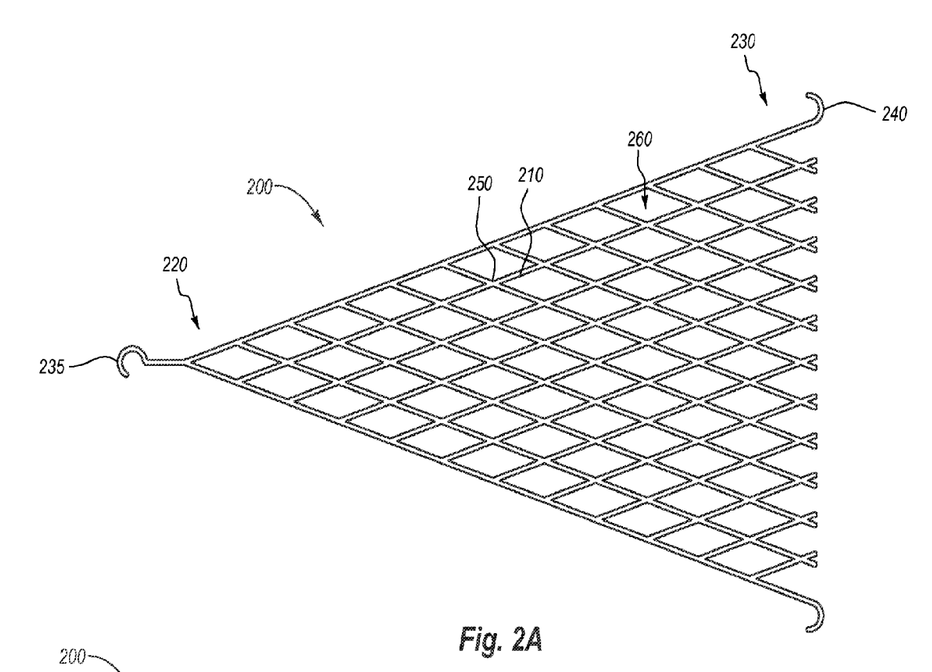
FIG. 2A illustrates a body lumen filter in an deployed state according to one example.

FIG. 2A illustrates a body lumen filter 200 in a deployed state according to one example. In at least one example, the body lumen filter 200 includes expandable struts 210 that extend at least partially between a first end 220 and a second end 230. In at least one example, the expandable struts 210 can be mechanically expanded by an expansion member, such as a balloon or other expansion member. In other examples the expandable struts 210 can be formed of a resilient material that can resiliently expand from a pre-deployed state to a deployed state due to the resilient nature of the material. For ease of reference, expandable struts 210 formed of a resilient material will be described below.

An engagement feature 235, such as a hook, is shown coupled to the first end 220. The engagement feature 235 is configured to engage a similar feature in the deployment device 400 (FIG. 1). As will be discussed in more detail below, the engagement feature 235 can be used to draw the body lumen filter 200 through the crimping device 300 (FIG. 3) and/or draw the body lumen filter 200 into the deployment device 400 during a retrieval operation. While a hook-type engagement feature is shown, it will be appreciated that any type of engagement feature may be utilized, such as a looped portion, a socket, positive engagement features, or other types of features that are configured to be selectively engaged by a corresponding feature on another device or assembly.

With continuing reference to FIG. 2A, the body lumen filter 200 can also include at least one anchor 240 coupled to the second end 230. In the illustrated example, anchors 240 are secured to the expandable struts 210 on the second end 230. The anchors 240 engage a vessel wall when the body lumen filter 200 is deployed to help maintain the vascular device 200 at the intended position within the body vessel. The anchors 240 can have any configuration or can be omitted as desired.

Figure 2B:
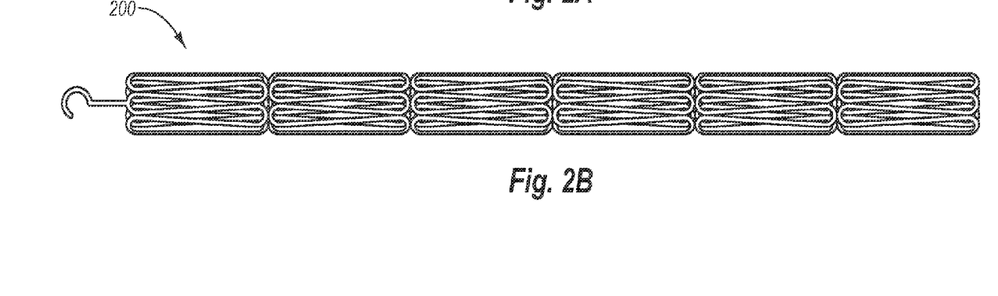
FIG. 2B illustrates the body lumen filter of FIG. 2A in a pre-deployed state.

FIG. 2B illustrates the body lumen filter 200 of FIG. 2A in a pre-deployed state. In at least one example, the body lumen filter 200 moves from the deployed state of FIG. 2A to the pre-deployed state as junctions 250 move from separated positions illustrated in FIG. 2A to the proximate positions as illustrated in FIG. 2B as the expandable struts 210 deflect. In particular, the expandable struts 210 are interconnected in such a manner as to allow the body lumen filter 200 to be moved from the pre-deployed state illustrated in FIG. 2A to a deployed state illustrated in FIG. 2B. Further, the body lumen filter can be formed of a resilient material. Such a configuration can allow the device to move between the deployed or unstressed state illustrated in FIG. 2A and the stressed or pre-deployed state illustrated in FIG. 2B, in which the body lumen filter 200 is located within the deployment device 400 (FIG. 1).

A resilient body lumen filter 200 is illustrated. Embodiments of the endoprosthesis body can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM can be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; and cobalt-chromium-nickel; nickel-titanium platinum; nickel-titainum palladium or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of an endoprosthesis can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic. The alloy can be utilized having linear elastic properties or non-linear elastic properties.

An SMP is a shape-shifting plastic that can be fashioned into an endoprosthesis in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

An endoprosthesis body having at least one layer made of an SMM or suitable superelastic material and other suitable layers can be compressed or restrained in its delivery configuration within a delivery device using a sheath or similar restraint, and then deployed to its desired configuration at a deployment site by removal of the restraint as is known in the art. An endoprosthesis body made of a thermally-sensitive material can be deployed by exposure of the endoprosthesis to a sufficient temperature to facilitate expansion as is known in the art. It will be appreciated that the body lumen filter 200 can be mechanically expanded, such as by a balloon or other expanding device.

In at least one example, the memory shape of the body lumen filter 200 can be a deployed state, such as the shape illustrated in FIG. 2A and the body lumen filter 200 can be mechanically moved to a strained, pre-deployed state similar to the shape illustrated in FIG. 2B. Such a process can be described as crimping. The body lumen filter 200 can be crimped using the crimping device 300, which will now be discussed in more detail.

Figure 3A:
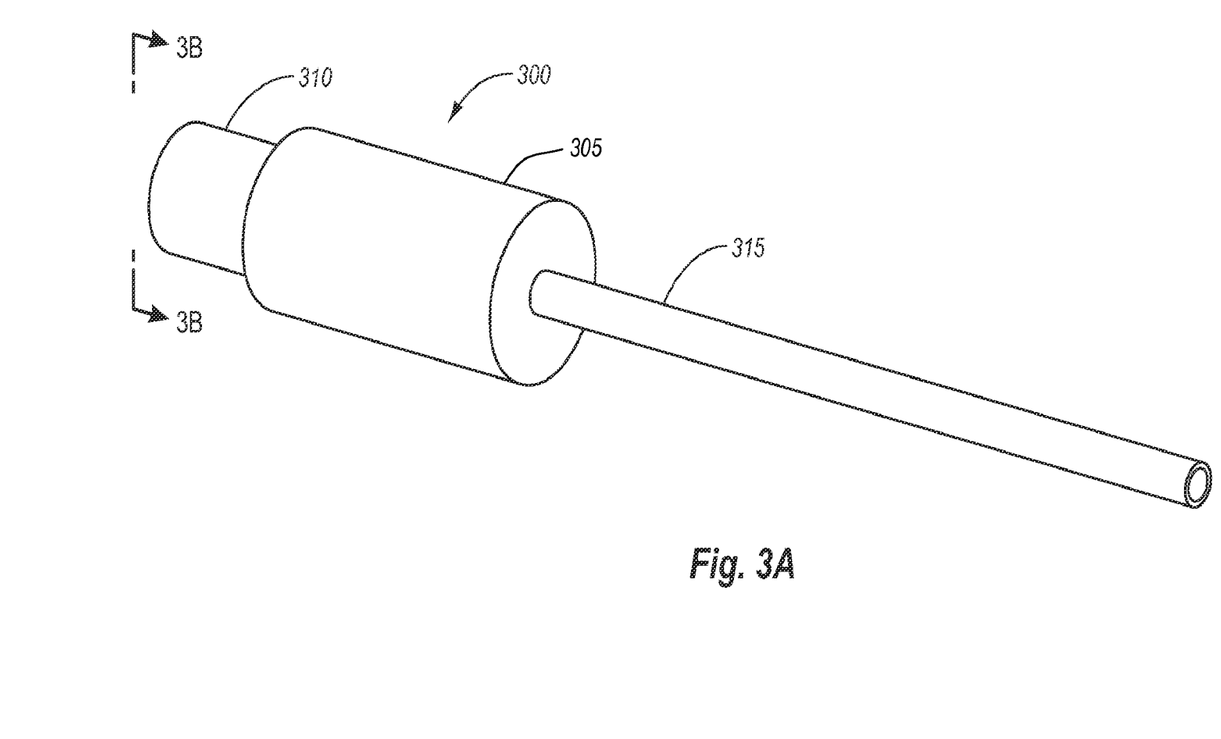
FIG. 3A illustrates a perspective view of a crimping device for loading a body lumen filter according to one example.

FIG. 3A illustrates the crimping device 300 in more detail. As illustrated in FIG. 3A, the crimping device 300 includes a base 305, a plug 310, and an exterior tube 315 operatively associated with the base 305. The base 305 is configured to support a body lumen filter. The plug 310 can then be brought into contact with the base 305. As will be discussed in more detail below, the base 305 and the plug 310 are configured to cooperate to apply even pressure to the surfaces of the body lumen filter 200 (FIG. 2) as the body lumen filter 200 is drawn through the base 305, through the exterior tube 315, and into a deployment device. The application of even pressure to the body lumen filter 200 can reduce undesired and/or unintended deformation of the body lumen filter 200, which can otherwise cause the strained or pre-deployed shape of the body lumen filter to deviate from the shape illustrated in FIG. 2B.

Figure 3B:
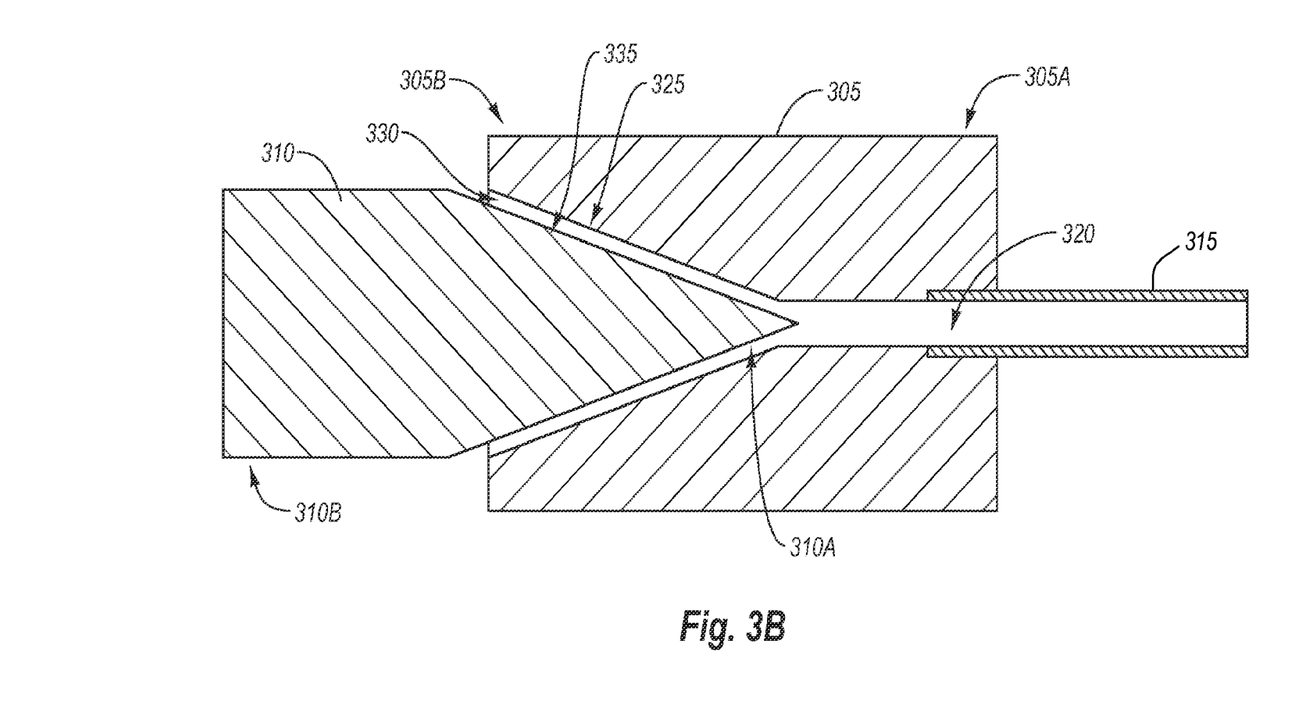
FIG. 3B illustrates a cross sectional view of the crimping device illustrated in FIG. 3A.

FIG. 3B illustrates a cross sectional view of the crimping device 300 illustrated in FIG. 3A. As illustrated in FIG. 3B, the base 305 includes a first end 305A and a second end 305B. A channel 320 is defined in the first end 305A. The channel 320 is in communication with the exterior tube 315.

The base 305 further includes an inner surface 325 formed therein that defines a recess 330. The recess 330 can be in communication with the channel 320. Further, the inner surface 325 may be dimensioned to closely correspond to the outer side of a body lumen filter, such as a vena cava filter. Such a configuration may allow a substantial portion of the outer surface of a body lumen filter to contact the inner surface 325. In the illustrated example, the inner surface 325 is configured to closely support the body lumen filter 200 (not shown) while the body lumen filter 200 is in the deployed state as shown in FIG. 2A.

The body lumen filter 200 is a tapered body lumen filter 200 that has a generally conical shape. It will be appreciated that the body lumen filter 200 may have any shape, such as a rounded shape, a partial elliptical shape, a parabolic shape, other shapes or combinations thereof. The recess 330 defined by the inner surface 325 may approximate the shapes described above as desired. Accordingly, in the illustrated example, the inner surface 325 has a negative conical shape.

The plug 310 includes a first end 310A and a second end 310B. In at least one example, the first end 310A may have a shape that is a positive complement to the second end 305B. Accordingly, the first end 310A of the plug 310 may have an outer surface 335 that has a generally conical shape. Such configuration can allow an inner surface of the body lumen filter 200 to come into substantially full contact with the outer surface 335. While conical shapes are described it will be appreciated that the plug, the inner surface and/or the body lumen filter can have partially conical cross sections that terminate in other than a tip, such as a stepped, flat, and/or rounded end.

In particular, the body lumen filter 200 (FIG. 2B) is positioned between the first end 310A of the plug 310 and the second end 305B of the base 305. Further, the first end 310A and second end 305B may be brought together such that the outer surface 335 of the plug contacts the inner surface of the body lumen filter 200 while the inner surface 325 of the base 305 contacts the outer surface of the body lumen filter 200. The base 305 and plug 310 may forced into contact with each other to apply a desired amount of pressure to the body lumen filter 200.

As previously introduced, the inner surface 325 and/or the outer surface 335 are configured to be brought into substantially full contact with the body lumen filter 200. In such a configuration, the pressure applied to the body lumen filter 200 as the base 305 and the plug 310 are brought toward each other may be evenly distributed on the surfaces of the body lumen filter 200. An even application of pressure to the body lumen filter 200 as it is crimped from a deployed state to a pre-deployed state may reduce or prevent deflection of various components in undesired or unintended directions to thereby maintain the body lumen filter 200 in a desired shape. The body lumen filter 200 is crimped by drawing the body lumen filter 200 through the channel 320. Accordingly, the channel 320 may be sized to move the body lumen filter 200 into a pre-deployed state to allow the body lumen filter to be located within the deployment device 400.

As will be discussed in more detail below, such a configuration may provide for even pressure on the surfaces of a body lumen filter as the body lumen filter is crimped during positioning of the body lumen filter within a deployment device. One example of a process for deploying a body lumen filter will now be described with references to FIGS. 4A-4G.

Figure 4A:
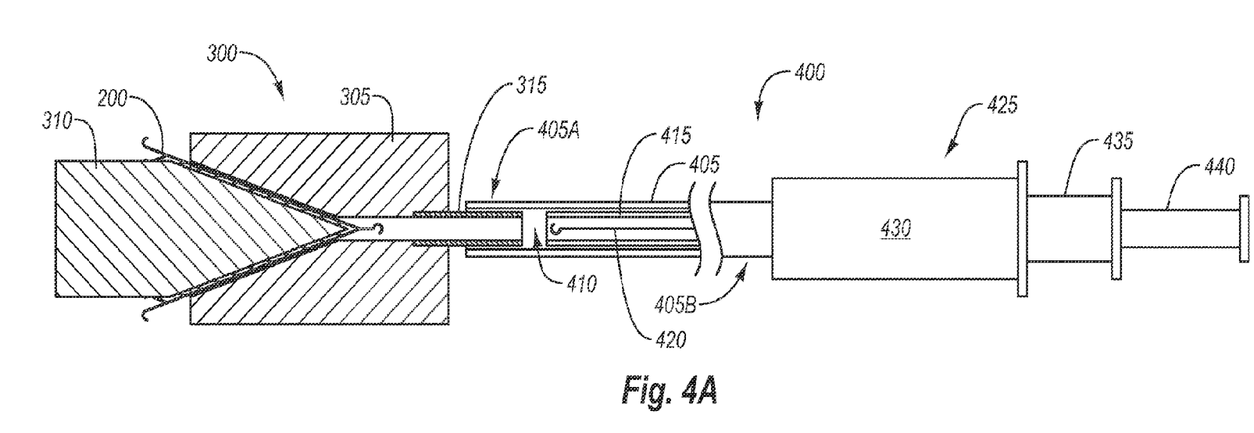
FIG. 4A illustrates a deployment device in proximity to a crimping device in which a body lumen filter is positioned according to one example.

FIG. 4A illustrates a deployment device 400 in proximity to a crimping device 300. Further, the body lumen filter 200 is positioned within the crimping device 300. The deployment device 400 includes an outer housing 405 having a distal end 405A and a proximal end 405B. The distal end 405A may have an atraumatic shape so as to reduce trauma associated with introducing the distal end 405A to a body vessel.

The outer housing 405 can have a generally tubular configuration to thereby define a lumen 410 therein. The lumen 410 can be sized to allow a deployment mechanism 415 to translate therein. Accordingly, the deployment mechanism 415 can be located at least partially within the outer housing 405. Further, the deployment mechanism 415 can have a generally tubular shape to thereby define a lumen therein (not shown). The lumen may be sized to allow a retrieval device 420 to translate relative to the deployment mechanism 415. The retrieval device 420 can be configured to engage body lumen filter 200. For example, the retrieval device 420 can have a shape that is complimentary to the engagement feature 235, such as another hook shape.

As illustrated in FIG. 4A, a process for loading a body lumen filter 200 into the deployment device 400 includes positioning the body lumen filter 200 in the crimping device 300. The process also includes positioning the deployment device 400 in proximity to the crimping device 300. In the illustrated example, the outer housing 405 receives the exterior tube 315 to thereby position the deployment mechanism 415, and the retrieval device 420 in particular in proximity to the exterior tube 315.

In the illustrated example, a proximal end 405B of the outer housing 405 is coupled to an actuation assembly 425 and to a main body 430 in particular. The actuation assembly 425 can further include one or more device(s) configured to move the deployment mechanism 415 relative to the outer housing 405 and/or to move the retrieval device 420 relative to the deployment mechanism 415. For example, the actuation assembly 425 can include a first plunger 435 coupled to the deployment mechanism 415 and a second plunger 440 coupled to the retrieval device 420. In particular, the first plunger 435 can be configured to translate relative to the main body 430 to thereby move the deployment mechanism 415 relative to the outer housing 405.

The second plunger 440 can be configured to translate with the first plunger 435 to maintain the relative position of the retrieval device 420 relative to the deployment mechanism 415 as desired. Further, the second plunger 440 can be configured to translate the relative to the first plunger 435 to provide relative movement between the retrieval device 420 and the deployment mechanism 415. Such a configuration can allow the first plunger 435 to be actuated to move both the deployment mechanism 415 and the retrieval device into position to initiate a step of loading the body lumen filter 200 into the deployment device 400, as will be described in more detail below.

Figure 4B:
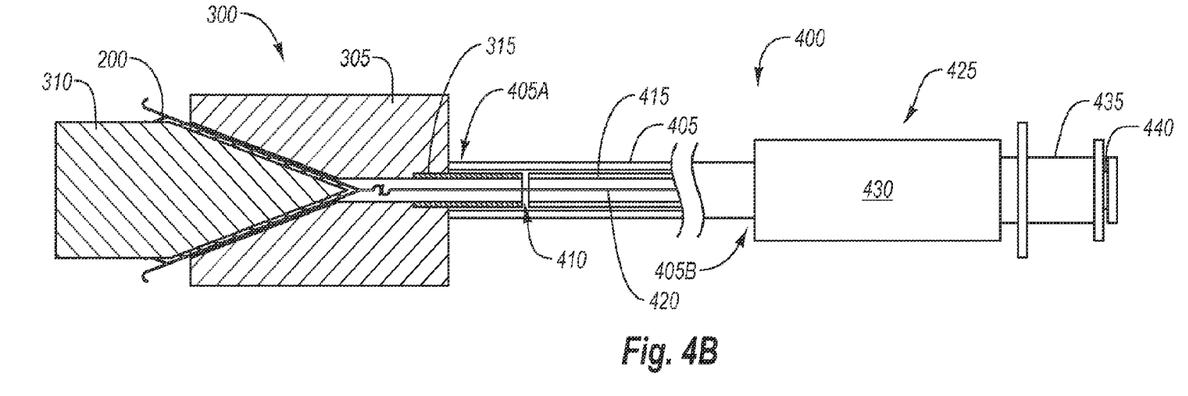
FIG. 4B illustrates engagement between the deployment device and the body lumen filter of FIG. 4A.

As previously introduced, one exemplary process for loading a body lumen filter 200 includes positioning the body lumen filter 200 in the crimping device 300 and positioning the deployment device 400 relative to the crimping device 300. As illustrated in FIG. 4B, a process for loading the body lumen filter 200 can also include moving a retrieval device 420 into engagement with the body lumen filter 200. In particular, the retrieval device 420 may be moved into engagement with the body lumen filter 200 by moving the second plunger 440 relative to the main body 430 and the first plunger 435. In at least one example, the retrieval device 420 can engage the engagement feature 235 by moving the retrieval device 420 past the engagement feature 235, rotating the retrieval device 420, and drawing the retrieval device 420 proximally to thereby engage the engagement feature 235. Engagement between the engagement feature 235 and the engagement device 400 can allow the body lumen filter to be drawn into the deployment device 300.

Figure 4C:
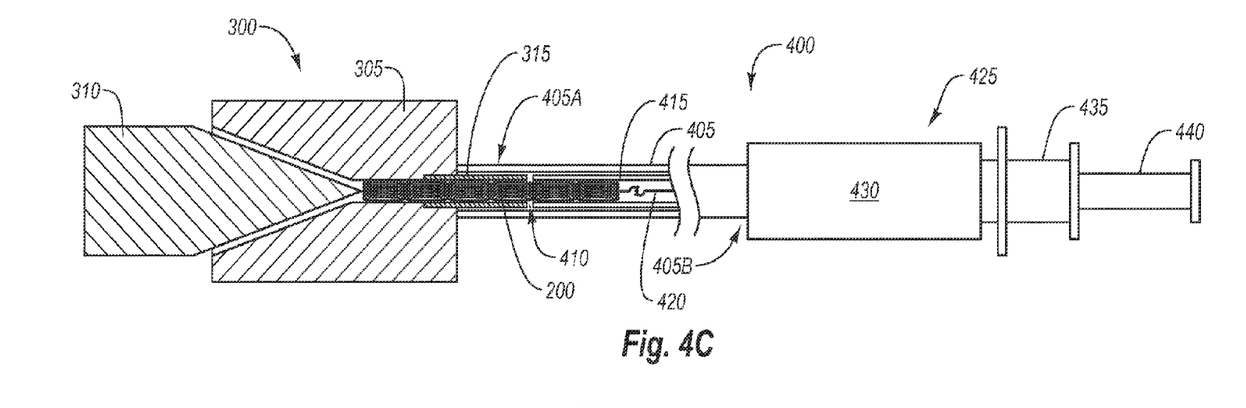
FIG. 4C illustrates engagement between the deployment device and the body lumen filter of FIG. 4A.

As illustrated in FIG. 4C, the process for loading the body lumen filter 200 into the deployment device 400 includes drawing the body lumen filter 200 through the crimping device 300. In particular, the second plunger 440 can be drawn proximally to draw the body lumen filter 200 through the channel 320, through the exterior tube 315, and into the deployment mechanism 415. As previously introduced, the crimping device 300 is configured to apply evenly distributed pressure to the body lumen filter 200 as the body lumen filter 200 is drawn through the crimping device 300 to the deployment device 400. The application of even pressure on the body lumen filter 200 can reduce the possibility that the body lumen filter 200 will be deformed during a loading process. In particular, relatively even pressure on body lumen filter 200 constrains the position of the structure of the body lumen filter 200 as it is drawn through the crimping device 300, which can help ensure proper functionality of the body lumen filter 200 during and after deployment.

Figure 4D:
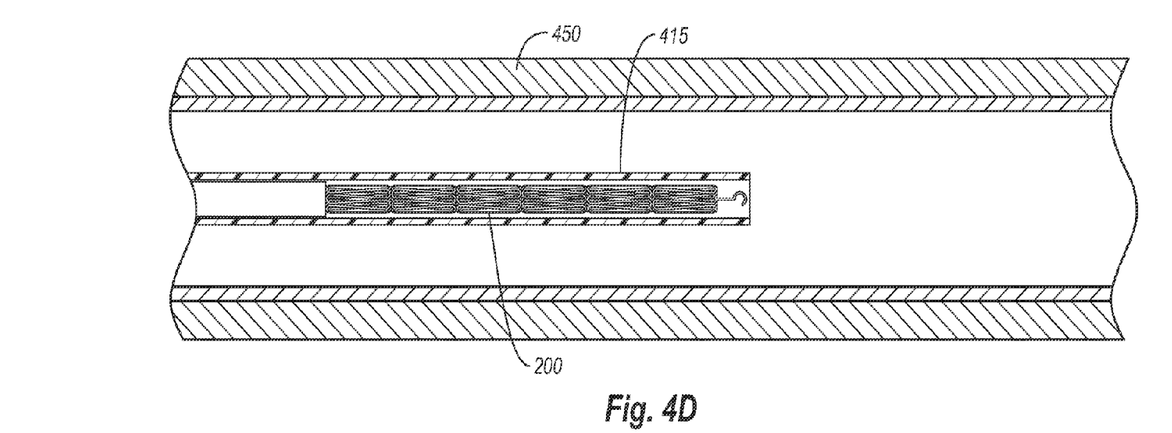
FIG. 4D illustrates a distal end of the deployment device positioned near a deployment site according to one example.
Figure 4E:
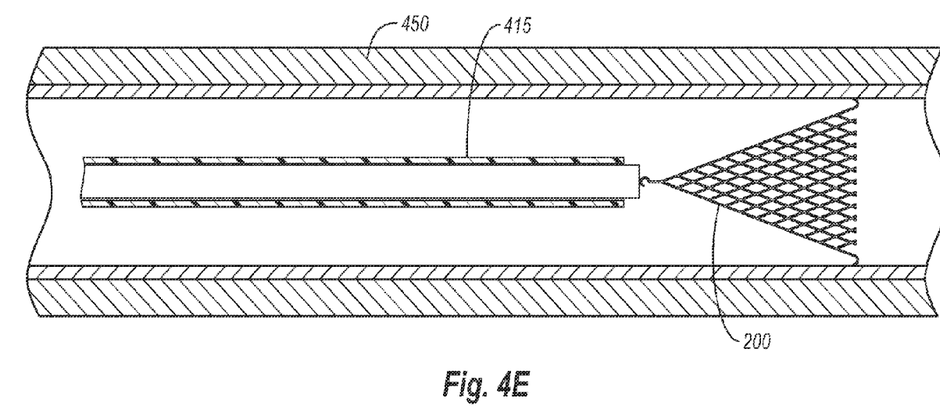
FIG. 4E illustrates the body lumen filter deployed at a deployment site according to one example.
Figure 4F:
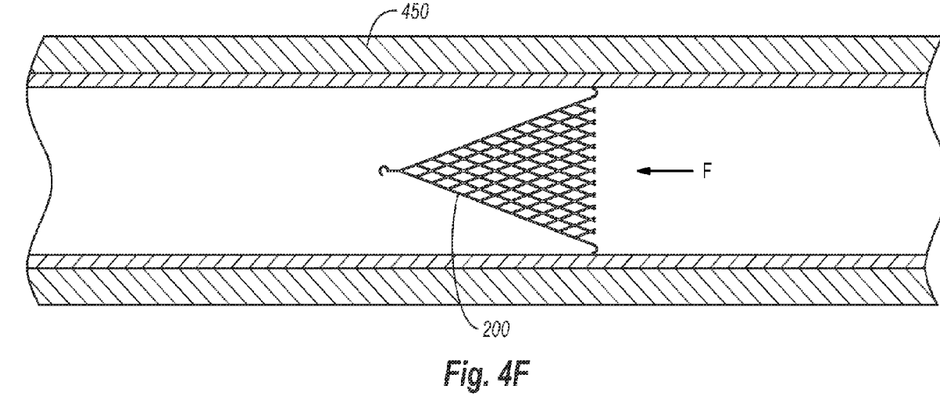
FIG. 4F illustrates the body lumen filter in position at the deployment site of FIG. 4F.

FIGS. 4D-4F illustrate deployment of a body lumen filter 200 according to one example. In particular, FIG. 4D illustrates the body lumen filter 200 located within the deployment device 400 used to deploy the body lumen filter 200 into a body lumen 450. To deploy the body lumen filter 200, the deployment device 400 is moved to a desired location within a body lumen 450 by using a catheter or other well-known techniques. Once the deployment device 400 is at the desired location, the deployment mechanism 415 is advanced distally relative to the outer housing 405, thereby driving the body lumen filter 200 from the distal end 405B of the outer housing 405 toward the desired location. In another example, the deployment device 400 may be advanced to the desired location, the delivery mechanism 415 may be advanced distally to abut the body lumen filter 200, the housing 225 may be retracted to deploy the body lumen filter 200, or combinations thereof. In another example, the deployment device 400 may be advanced to the desired location, the delivery mechanism 415 may be advanced distally to abut the body lumen filter 100, the housing 225 may be retracted to deploy the body lumen filter 100, or combinations thereof.

As the body lumen filter 200 is advanced beyond the distal end 405B, the body lumen filter 200 moves towards the deployed state. For instance, when the body lumen filter 200 is formed from a shape memory material releasing the body lumen filter 200 from the distal end 405B of the outer housing 405 causes the body lumen filter 200 to transition to the deployed or unstressed state of FIG. 4E.

The body lumen filter 200 can be released from engagement with the engagement device 420 before, after, or concurrently as the body lumen filter 200 is driven from the deployment device. For example, the body lumen filter 200 can be released from the engagement device 420 by advancing the engagement device 420 proximally relative to the engagement feature 235 and rotating the engagement device 420 relative to the engagement feature 235 to thereby disengage the engagement device 420 from the engagement feature 235.

Once the body lumen filter 200 is freed from engagement with the deployment device 400, the vascular device 200 can be left to filter a blood flow, as illustrated in FIG. 4F. In particular, as the body lumen filter 200 is moved to the deployed state, the expandable struts 210 can be displaced to provide filtering openings 260. As illustrated in FIGS. 2A and 4F, the filtering openings 260 can be sized to prevent particulates, such as an embolus, from passing through the body lumen filter 200.

While the embolus is trapped against body lumen filter 200, blood will continue to flow over the embolus. The flow of blood over the embolus can dissolve the embolus through the body's lysing process. The blood flow F exerts a fluid force on the body lumen filter 200 that would tend to move the body lumen filter 200 in the direction of the blood flow F. The anchors 240 counter this force to maintain the body lumen filter 200 in an intended deployment location.

Figure 4G:
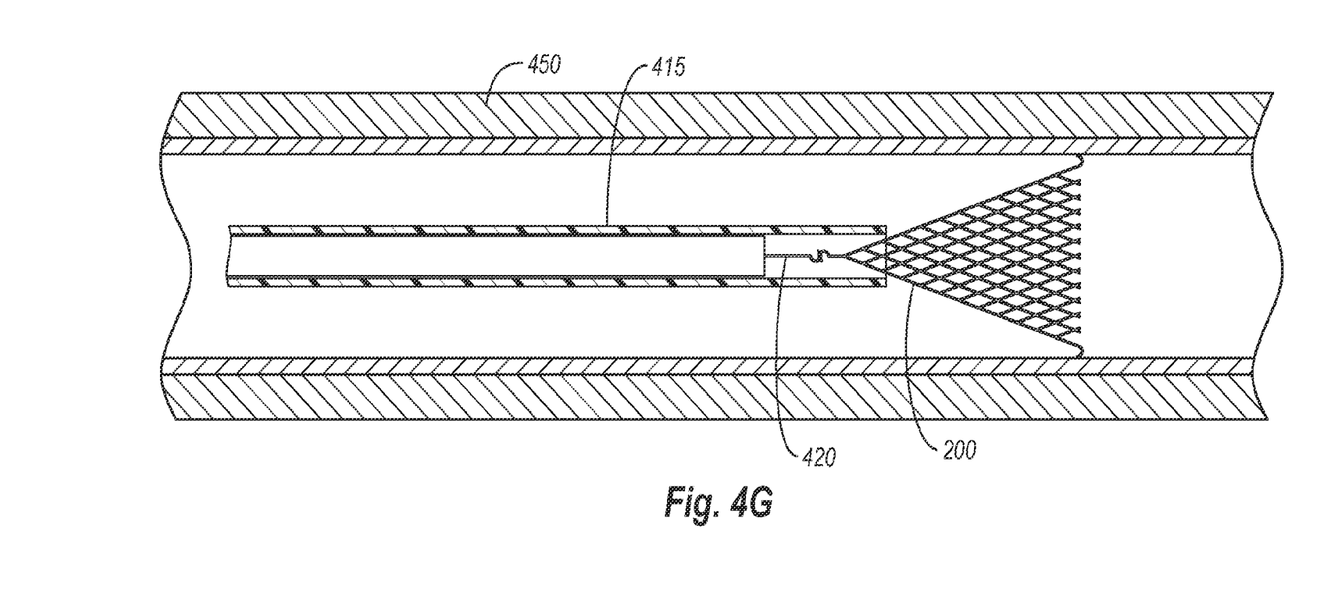
FIG. 4G illustrates retrieval of the body lumen filter according to one example.

At some point, it may be desirable to retrieve the body lumen filter 200. FIG. 4G illustrates a step for retrieving the body lumen filter 200. As illustrated in FIG. 4G, retrieving the body lumen filter 200 can include positioning the deployment device 400 such that the outer housing 405 is positioned in proximity to the body lumen filter 200. Thereafter, the retrieval device 420 can be moved into engagement with the engagement feature 235 on the body lumen filter 200. Thereafter, the second plunger 440 and/or the first plunger 435 (both shown in FIGS. 4A-4C) can be drawn proximally to thereby draw the body lumen filter 200 into the distal end 405A of the outer housing 405 and/or into the delivery mechanism 415. Once the body lumen filter 200 is located within the delivery mechanism 415 and/or the outer housing 405, the deployment device 400 can be removed to thereby complete retrieval of the body lumen filter 200.

Accordingly, systems, methods, and devices have been provided herein for loading, deploying, and/or retrieving a body lumen filter. As discussed, the systems, methods, and devices can be configured to reduce unintended deformation of the body lumen filter as the body lumen filter is loaded into a deployment device. Further, the deployment device and body lumen filter can be configured to retrieve the body lumen filter if desired.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for crimping a body lumen filter, comprising:
a plug having an outer angled surface;
a tube having a lumen formed therein; and
a base having a channel extending from a first end of the base towards a second end of the base, the tube being operatively associated with the base and received within a portion of the channel, a remainder of the channel extending from the tube towards the second end, the base further including an inner angled surface in communication with the channel and extending away from an end of the channel opposite to the end operatively associated with the outer tube towards the second end, wherein at least a portion of the inner angled surface and the outer angled surface are complimentary.

2. The device of claim 1, wherein the channel is sized to collapse a body lumen filter as the body lumen filter is drawn therethrough.

3. The device of claim 1, wherein the lumen is in communication with the channel.

4. The device of claim 1, wherein the plug has a generally conical shape.

5. A system, comprising:
a crimping device having:
a plug having an outer angled surface;
a tube having a lumen; and
a base having a channel extending from a first end of the base towards a second end of the base, the tube extending from the first end and being received within a portion of the channel, a remainder of the channel extending from an end of the tube towards the second end and having a uniform cross-section, the base further including an inner angled surface in communication with the channel and extending from an end of the channel, opposite to the end operatively associated with the outer tube, towards the second end;
a body lumen filter being configured to be located at least partially between the base and the plug; and
a deployment device having an outer tube and a retrieval device, the retrieval device being configured to draw the body lumen filter through the channel and at least partially into the outer tube, wherein the crimping device is configured to apply even pressure to the body lumen filter between the base and the plug as the body lumen filter is drawn through the channel.

6. The system of claim 5, wherein at least a portion of the plug has a shape complimentary to a corresponding portion of the base.

7. The system of claim 5, wherein the body lumen filter includes an engagement feature configured to be engaged by the retrieval device.

8. The system of claim 5, wherein the body lumen filter includes a first end and a second end, the first end being narrower than the second end.

9. The system of claim 5, wherein the body lumen filter is formed from a resilient material.

10. The system of claim 5, wherein the deployment device includes an inner tube configured to translate within the outer tube.

11. The system of claim 10, wherein the retrieval device is configured to translate within the inner tube.

12. The system of claim 5, further comprising an exterior tube having a lumen defined therein, the exterior tube being coupled to the base such that the lumen is in communication with the channel.

13. The system of claim 12, wherein the exterior tube is sized to be at least partially received within the outer tube of the retrieval device.

14. The system of claim 13, wherein the plug is at least partially conically shaped.

15. The system of claim 5, wherein the retrieval device includes a hook.

16. A method of loading a body lumen filter, comprising:
positioning a body lumen filter in a crimping device at least partially between a plug and a base;
pressing the body lumen filter between the plug and the base;
drawing the body lumen filter through a channel in the crimping device while pressing the body lumen filter, the channel extending from a first end of the base towards a second end of the base with a tube extending from the first end and being received within a portion of the channel, a remainder of the channel extending from an end of the tube towards the second end, a recess having an inner angled surface being in communication with the channel and extending from an end of the channel, opposite to the end operatively associated with the outer tube, towards the second end; and
drawing the body lumen filter into a deployment device.

17. The method of claim 16, wherein pressing the body lumen filter between the plug and the base includes applying pressure to the body lumen filter between an outer surface of the plug and an inner angled surface of the base.

18. The method of claim 16, wherein drawing the body lumen filter through a channel in the crimping device includes coupling an engagement feature coupled to the body lumen filter to a retrieval device of a deployment device.

19. The method of claim 16, further comprising drawing the body lumen filter into an outer tube of the deployment device.

20. The method of claim 19, further comprising a step of positioning the deployment device relative to the base by coupling the outer tube to the tube coupled to the base.

21. The method of claim 19, further comprising moving the body lumen filter to a deployment site with the deployment device and deploying the body lumen filter to a deployed position.

22. The method of claim 21, further comprising retrieving the body lumen filter by coupling the engagement feature to the retrieval device and drawing the body lumen filter at least partially into the outer tube.

* * * * *